(12) United States Patent
Solarz et al.

(10) Patent No.: US 8,575,576 B2
(45) Date of Patent: Nov. 5, 2013

(54) OPTICAL IMAGING SYSTEM WITH LASER DROPLET PLASMA ILLUMINATOR

(75) Inventors: Richard W. Solarz, Danville, CA (US); Stephane P. Durant, Mountain View, CA (US); Shiow-Hwei Hwang, San Ramon, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 246 days.

(21) Appl. No.: 13/026,926

(22) Filed: Feb. 14, 2011

(65) Prior Publication Data
US 2012/0205546 A1    Aug. 16, 2012

(51) Int. Cl.
  *G01J 3/10* (2006.01)
  *G01J 1/58* (2006.01)
(52) U.S. Cl.
  USPC ............. 250/504 R; 250/458.1; 250/459.1
(58) Field of Classification Search
  USPC ...................... 250/458.1, 459.1, 504 R
  See application file for complete search history.

(56) References Cited

U.S. PATENT DOCUMENTS

| 7,351,980 | B2 | 4/2008 | Lange |
| 7,599,470 | B2 | 10/2009 | Kloepfel et al. |
| 7,705,331 | B1 | 4/2010 | Kirk et al. |
| 2003/0067598 | A1 | 4/2003 | Tomie et al. |
| 2004/0170252 | A1 | 9/2004 | Richardson |
| 2006/0103725 | A1 | 5/2006 | Brown et al. |
| 2007/0228288 | A1 | 10/2007 | Smith et al. |
| 2010/0188655 | A1 | 7/2010 | Brown et al. |
| 2010/0188738 | A1 | 7/2010 | Epple et al. |
| 2010/0213395 | A1* | 8/2010 | Ueno et al. ............... 250/504 R |
| 2011/0141865 | A1* | 6/2011 | Senekerimyan et al. .. 369/47.15 |
| 2011/0240890 | A1* | 10/2011 | Govindaraju et al. .... 250/504 R |

FOREIGN PATENT DOCUMENTS

WO        2010148293 A2    12/2010

OTHER PUBLICATIONS

International Search Report and Written Opinion mailed on Sep. 17, 2012, for PCT Application No. PCT/US2012/023149 filed on Jan. 30, 2012, by KLA-Tencor Corporation, 13 pages.

* cited by examiner

*Primary Examiner* — Mark R Gaworecki
(74) *Attorney, Agent, or Firm* — Spano Law Group; Joseph S. Spano

(57) ABSTRACT

A wafer inspection system includes a laser droplet plasma (LDP) light source that generates light with sufficient radiance to enable bright field inspection at wavelengths down to 40 nanometers. Light generated by the LDP source is directed to the wafer and light from the illuminated wafer is collected by a high NA objective with all reflective elements. A detector detects the collected light for further image processing. The LDP source includes a droplet generator that dispenses droplets of a feed material. An excitation light generated by a laser is focused on a droplet of the feed material. The interaction of the excitation light with the droplet generates a plasma that emits illumination light with a radiance of at least 10 W/mm$^2$-sr within a spectral range from 40 nanometers to 200 nanometers.

27 Claims, 15 Drawing Sheets

OPTICAL IMAGING SYSTEM WITH LASER DROPLET PLASMA ILLUMINATOR

TECHNICAL FIELD

The described embodiments relate to illumination sources and systems for microscopy.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. When inspecting specular or quasi-specular surfaces such as semiconductor wafers a bright field (BF) modality may be used, both to perform patterned wafer inspection and defect review. In BF inspection systems, collection optics are positioned such that the collection optics capture a substantial portion of the light specularly reflected by the surface under inspection. Viable BF inspection systems require high radiance illumination and a high numerical aperture (NA) to maximize the defect sensitivity of the system.

Current wafer inspection systems typically employ illumination sources of deep ultraviolet (DUV) radiation with wavelengths as short as 260 nanometers with a high numerical aperture (NA). In general, the defect sensitivity of an inspection system is proportional to the wavelength of the illumination light divided by the NA of the objective. Without further improvement in NA, the overall defect sensitivity of current inspection tools is limited by the wavelength of the illumination source.

In the case of broad band imaging tools, the illumination light is typically delivered to the wafer through a catadioptric objective (combination of reflective and refractive optical elements). In the case of narrow band imaging tools, the illumination light is typically delivered to the wafer through transmissive objectives or microscopes. Thus, current BF inspection tools employ optical sub-systems that include refractive optical elements.

In some examples of BF inspection systems, illumination light may provided by an arc lamp. For example, electrode based, relatively high intensity discharge arc lamps are used in inspection systems. However, these light sources have a number of disadvantages. For example, electrode based, relatively high intensity discharge arc lamps have radiance limits and power limits due to electrostatic constraints on current density from the electrodes, the limited emissivity of gases as black body emitters, the relatively rapid erosion of electrodes made from refractory materials due to the presence of relatively large current densities at the cathodes, and the inability to control dopants (which can lower the operating temperature of the refractory cathodes) for relatively long periods of time at the required emission current.

In some other examples, illumination light may provided directly by a laser. One approach has been the harmonic upconversion of longer wavelength sources to shorter wavelengths. However, the average power that can be reliably sustained is typically below one Watt; far below the ten to one hundred watts average power required for high throughput, high resolution BF wafer inspection. In another example, excimer lasers have been developed with higher average power, but the kinetics of excimer lasers at short wavelengths limit these devices to low repetition rates (e.g., several kHz or less). In addition, these lasers are very short pulse lasers (e.g., a few nanoseconds). The combination of a low repetition rate and a short pulse duration results in a fluence delivered to a wafer under inspection that far exceeds the damage limit of materials used to construct the wafer (e.g., $SiO_2$, Si, metals, and resist materials).

In some other examples, illumination light may be provided by an incoherent light source pumped by a laser (e.g., laser sustained plasma). Laser sustained plasmas are produced in high pressure bulbs surrounded by a working gas at lower temperature than the laser plasma. While substantial radiance improvements are obtained with laser sustained plasmas, the temperature of these plasmas is generally limited by the photophysical and kinetic processes within these lamps. Pure atomic and ionic emission in these plasmas is generally confined to wavelengths longer than 200 nm when using either continuous wavelength or pulsed pump sources. Excimer emission can be arranged in laser sustained plasmas for wavelength emission at 171 nm (e.g., xenon excimer emission), but these sources are typically narrow band, limited in power, and limited in radiance. Excimer emission at 171 nanometers optimizes at low pressures (e.g., 3 bar and below), and the power of 171 nm emission is greatly diminished at higher pressures needed for high radiance. As a consequence, a simple gas mixture in a high pressure bulb is only able to sustain wavelength coverage above 200 nm with sufficient radiance and average power to support high throughput, high resolution BF wafer inspection.

Development efforts in the area of extreme ultraviolet (EUV) lithography are focused on light sources that emit narrowband radiation centered at 13 nanometers at high power levels (e.g., 210 watts of average power at the intermediate focus of the illuminator). Light sources for EUV lithography have been developed using a laser droplet plasma architecture. For example, xenon, tin, an lithium droplet targets operating at pulse repetition frequencies of 100 kHz and higher are pumped by $CO_2$ coherent sources. The realized light is high power (e.g., 210 watts of average power at the intermediate focus of the illuminator is the goal for lithography tools at 13 nanometers). However, the materials that comprise a semiconductor wafer exhibit practically no reflectivity to narrowband light at 13 nanometers.

Shorter wavelength illumination sources with the required radiance and average power for BF inspection applications are required. Preferably, such a source should be continuous wavelength or close to continuous wavelength to avoid damage to illuminated specimens. Furthermore, manufacturable objectives and sensors compatible with such sources are required to realize a viable BF inspection system.

SUMMARY

A bright field wafer inspection system includes a laser droplet plasma (LDP) light source that generates light with sufficient radiance to inspect at wavelengths down to 40 nanometers. The LDP source includes a droplet generator that dispenses droplets of a feed material. An excitation light generated by a laser is focused on a droplet of the feed material. The interaction of the excitation light with the droplet generates a plasma that emits illumination light with a radiance of at least 10 W/mm$^2$-sr, and in some instances higher than 1 kW/mm2-sr, within a spectral range from 40 nanometers to 200 nanometers.

In a first embodiment, the LDP light source generates illumination light with a radiance of at least 10 W/mm$^2$-sr, and in some instances higher than 1 kW/mm2-sr), within a spectral range from 100 nanometers to 200 nanometers. A solid state laser with a wavelength of approximately one micron and pulse duration between 1 and 40 nanoseconds generates an excitation light with a pulse energy between 1 and 20 milliJoules. At these energy levels a droplet of suitable feed material of approximately 50 microns in size may be made to ionize into a plasma with a plasma temperature of 4-10 eV. Suitable feed materials include, but are not limited to Ga, In, C, Si, Zn, Cu, and O. In particular, suitable feed materials may include any of Ga, In, C, Si, Zn, Cu, and O in hydride or oxide molecular compositions. In one non-limiting example, suitable feed materials may include $SiH_4$, $SiO_2$, $O_2$, $CH_4$, $H_2O$, and $CO_2$. In other examples, suitable feed materials include the rare gases, the alkalis, and the halides.

An inspection system operable to inspect a semiconductor wafer at these wavelengths includes optical elements to efficiently collect the illumination light emitted by the plasma, direct the illumination light to a wafer, and collect and magnify imaging light emitted from the wafer. All-reflective optical subsystems are presented that are constructed from $MgF_2$ overcoated aluminum to minimize absorption losses.

In a second embodiment, the LDP light source generates illumination light with a radiance of at least 10 W/mm$^2$-sr within a spectral range from 40 nanometers to 55 nanometers. A solid state laser with a wavelength of approximately one micron and a pulse duration between 1 and 40 nanoseconds generates an excitation light with a pulse energy between 1 and 20 milliJoules. At these energy levels a droplet of suitable feed material of approximately 50 microns in size may be made to ionize into a plasma with a plasma temperature of 8-20 eV. Suitable feed materials include, but are not limited to the rare gases, alkali metals, and the metal halides.

An inspection system operable to inspect a semiconductor wafer at these wavelengths includes optical elements to efficiently collect the illumination light emitted by the plasma, direct the illumination light to a wafer, and collect and magnify imaging light emitted from the wafer. All reflective optical subsystems are presented that include multi-layer Bragg mirrors with alternating layers of Scandium and Silicon to minimize absorption losses.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein, as defined solely by the claims, will become apparent in the non-limiting detailed description set forth herein.

DETAILED DESCRIPTION

Reference will now be made in detail to background examples and some embodiments of the invention, examples of which are illustrated in the accompanying drawings.

Figure 1:
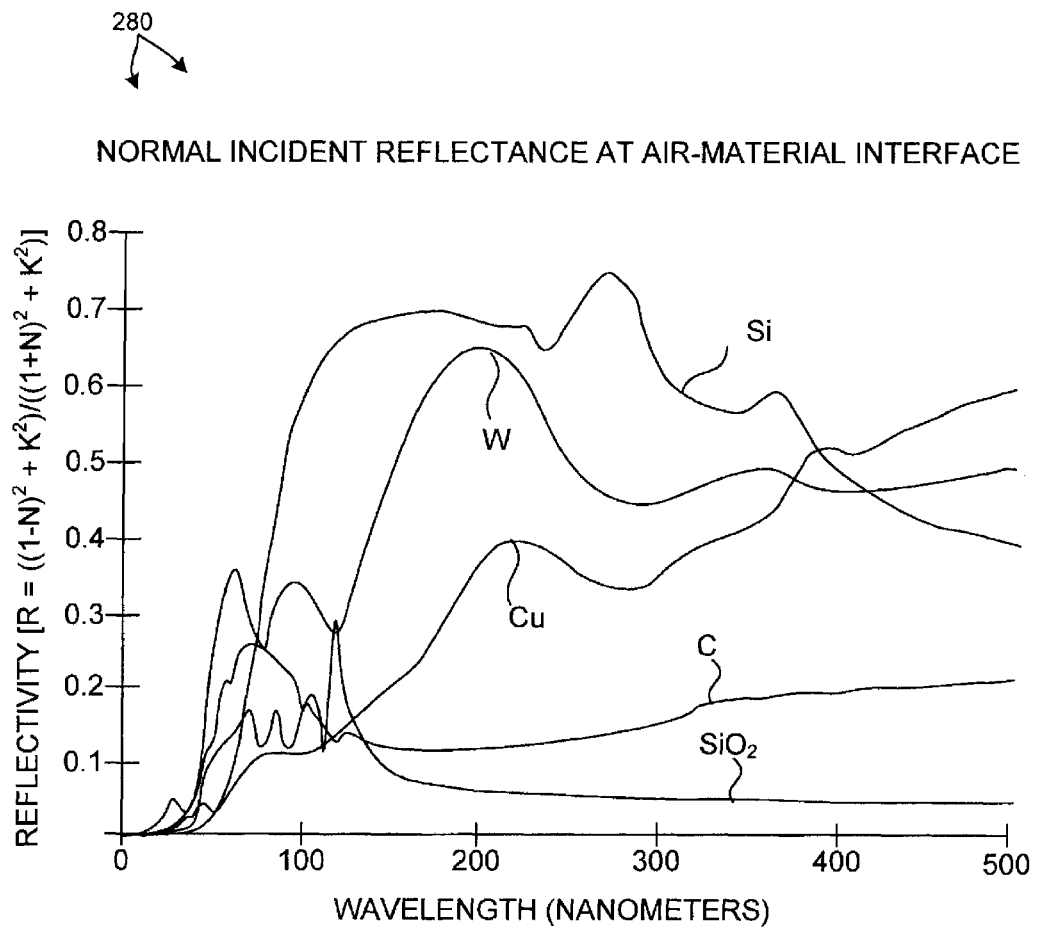
FIG. 1 is a plot illustrative of the reflectance properties of materials commonly used in semiconductor device fabrication.

FIG. 1 illustrates a plot 280 indicative of the normal incident reflectance at the air-material interface of several materials commonly utilized in the fabrication of a semiconductor device. FIG. 1 illustrates the reflectivity of silicon (Si), silicon dioxide ($SiO_2$), copper (Cu), carbon (C), and tungsten (W) as a function of the wavelength of light incident to each material. In general, the reflectivity of each of these materials in the 100 nanometer to 200 nanometer range of wavelengths is similar to the reflectivity at longer wavelengths (e.g., wavelengths greater than 260 nanometers employed in current BF inspection systems). Thus, from the perspective of reflected light, illumination sources in the 100 nanometer to 200 nanometer range should not be significantly disadvantaged relative to sources emitting above 260 nanometers. The reflectivity near 47 nanometers is approximately 5%. Although significantly lower than the range between 100 nanometers and 200 nanometers, the response of these materials to illumination light in a narrowband range (e.g., 10 nanometer waveband) centered near 47 nanometers is still useful for inspection purposes.

A source of incoherent radiation including emission in a spectral region between 40 nanometers and 200 nanometers with a radiance greater than 10 W/mm²-sr is disclosed. In addition, exemplary wafer inspection systems utilizing the light source are disclosed. The light source includes a feed material dispensed as a sequence of droplets by a droplet generator. In some embodiments, the output of a laser is focused onto a droplet to create a plasma that emits light in a spectral region between 40 nanometers and 55 nanometers. In some other embodiments, the output of a laser is focused onto a droplet to create a plasma that emits light in a spectral region between 100 nanometers and 200 nanometers.

Figure 2:
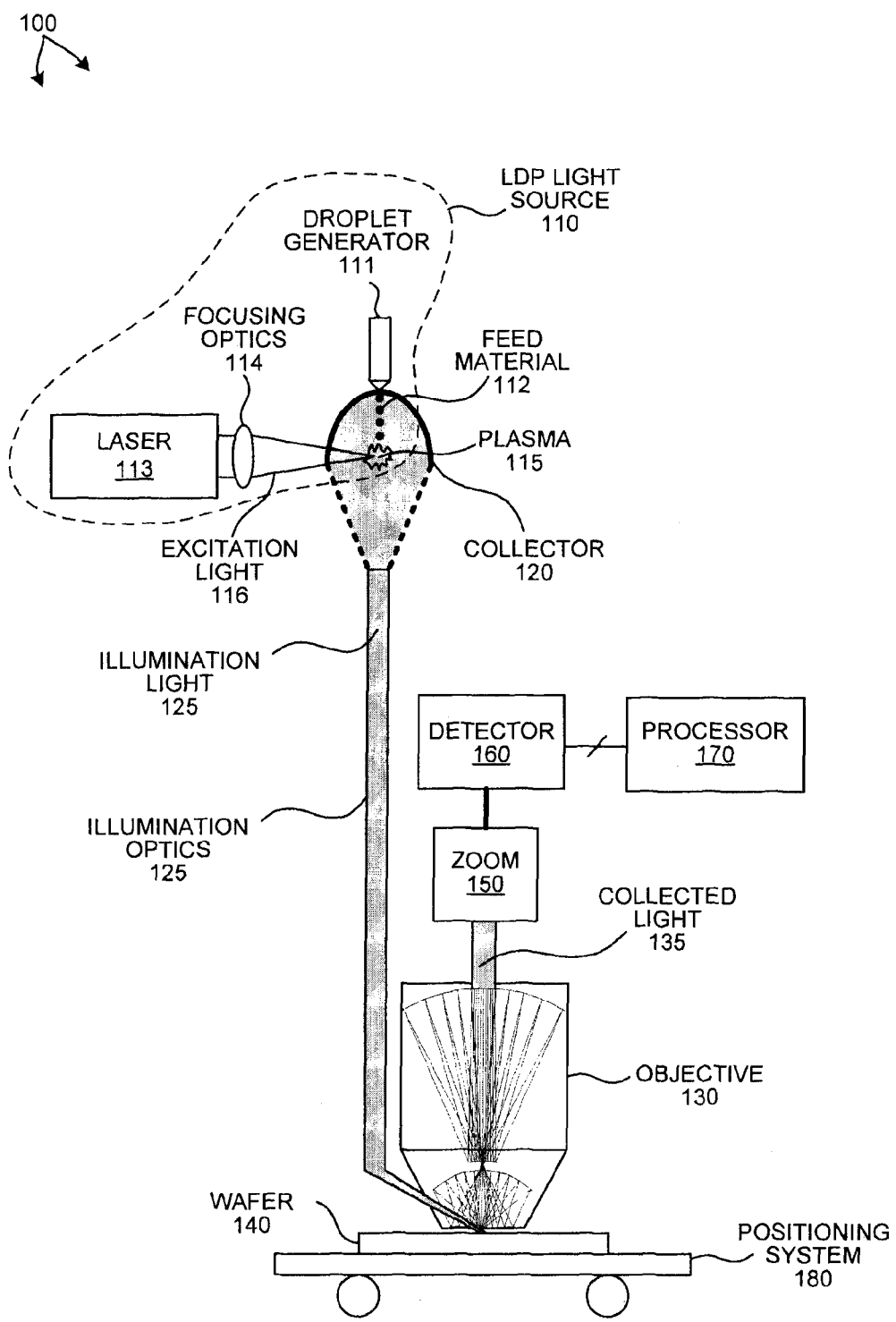
FIG. 2 is a simplified diagram illustrative of a wafer inspection system 100 that includes a laser droplet plasma light source 110.

FIG. 2 illustrates a wafer inspection system 100 configured to inspect a wafer using illumination light in a spectral region between 40 nanometers and 200 nanometers. Wafer inspection system 100 includes a laser droplet plasma (LDP) light source 110 that generates illumination light in a spectral region between 40 nanometers and 200 nanometers. The illumination light is transmitted to wafer 140 and imaging objective 130 directs the reflected illumination light to detector 160. In some embodiments, illumination light generated by light source 110 is gathered by a collector 120 and transmitted by at least one illumination optic 125 to objective 130. In some embodiments the illumination optics 125 and the imaging objective 130 may be comprised of primarily the same elements and be substantially the same. In some other embodiments, illumination light generated by light source 110 is gathered by a collector 120 and transmitted by at least one illumination optic 125 directly to specimen 140 without first being directed through the elements of the imaging objective 130. Specimen 140 emits an imaging light in response to illumination light incident to specimen 140. The imaging light is, however, still gathered as a collected light and magnified by the imaging objective 130. In some embodiments, the objective 130 transmits the collected light to imaging detector 160 via zoom optics 150 that further magnify the image collected from specimen 140. Detector 160 receives the imaged light and converts the light to electrical signals. Detector 160 communicates the electrical signals to processor 170 for further image processing by processor 170. In some embodiments, specimen 140 is affixed to a positioning system 180 by a vacuum or electrostatic mechanism. In this manner, specimen 140 is flexibly positioned under objective 130.

In one aspect, LDP light source 110 emits broadband radiation in a spectral region between 40 nanometers and 200 nanometers with a radiance greater than 10 w/mm2-sr within the spectral region between 40 nanometers and 200 nanometers. Such emission is suitable for BF inspection of patterned semiconductor wafers imaged in broadband optical microscopes that can image over a field of view from 100 microns to a few millimeters with high throughput (e.g., at least 5 wafers/hour).

In some embodiments, LDP light source 110 generates a plasma 115 in the 4-10 eV temperature range that emits light with a radiance greater than 10 W/mm²-sr in a spectral region between 100 nanometers and 200 nanometers. In some other embodiments, LDP light source 110 generates a plasma 115 in the 8-20 eV temperature range that emits light with a radiance of at least 10 W/mm²-sr in a spectral region between 40 nanometers and 55 nanometers. In some embodiments a radiance as high as 1 kW/mm²-sr may be achieved.

As depicted in FIG. 2, LDP light source 110 includes a droplet generator 111 and a laser 113. Droplet generator 111 dispenses a sequence of droplets of a feed material 112. Laser 113 generates an excitation light 116 that is focused on a droplet of the feed material. The excitation light causes the droplet of feed material to ionize to form a plasma that emits an illumination light. In some embodiments, droplet generator 111 is a high frequency fluid dispenser based on commercially available ink jet technology. In one example, droplet generator 111 dispenses a sequence of nominally 50 micron droplets of a feed material 112 at a rate between 50 and 200 kilohertz. In other examples, droplet sizes may vary between 25 and 100 microns. In some embodiments, laser 113 is a solid state laser with a pulse duration between 1 and 40 nanoseconds, and more specifically, between 5 and 20 nanoseconds. The output wavelength of solid state laser 113 is approximately 1 micrometer (e.g., between 0.9 and 1.1 micrometers). Solid state laser 113 generates between 1 and 20 milliJoules per pulse, and more specifically, between 3 and 10 milliJoules per pulse. In some embodiments, solid state laser 113 is a Ytterbium (Yb) based solid state laser. In some other embodiments, solid state laser 113 is a Neodymium (Nb) based solid state laser.

In some embodiments, a small charge may be applied to particles of each droplet dispensed by the droplet generator 111 and a controllable electric field may be introduced in the droplet flight path. In this manner, each droplet may be steered by a controlled electric field to precisely locate each droplet within the excitation light path generated by laser 113.

To obtain an illumination light from a laser droplet plasma with a radiance greater than 10 w/mm²-sr in a spectral region between 40 nanometers and 200 nanometers, a suitable material must be selected and the material must be heated to a sufficiently high plasma temperature at a sufficiently high plasma density. The temperature of a droplet plasma can be determined by matching the number of photons in the ionizing laser pulse to the number of atoms in the pellet or droplet being excited by the laser 113. For example, liquid copper droplets used as targets for laser plasma 115 can produce copious amounts of broad band 100-200 nm radiation when excited to 4 eV (or higher) plasma temperatures. These plasma temperatures may be obtained with a laser pulse energy of approximately 5-10 mJ per pulse or in ranges near these pulse energies. To ignite the plasma it is necessary that a fluence of near 5e9 to 1e10 W/cm2 be supplied. Thus, to both ignite and sustain the plasma, the laser 113 should have a pulse length between 1 and 40 nanoseconds. Commercially available thin-disk lasers manufactured by TRUMPF Group (Germany) are suitable for this purpose. Although commercially available thin-disk lasers may operate to ignite and sustain plasma 115, a modification of this laser type from a simple oscillator to an injection seeded master oscillator power amplifier (MOPA) architecture more closely generates the desired operating conditions.

Figure 3:
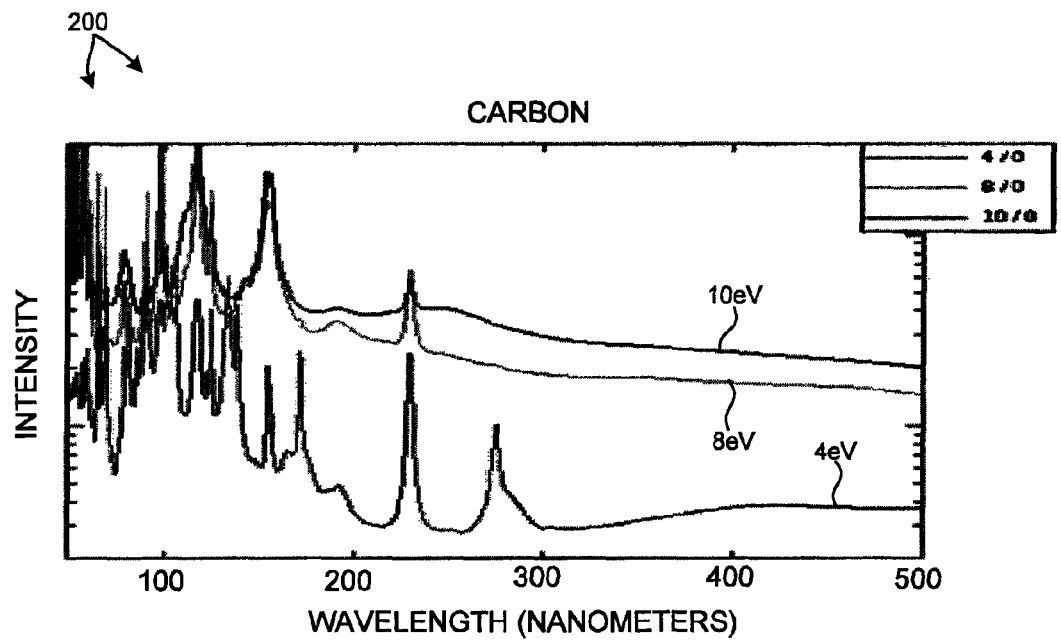
FIG. 3 is a plot of simulation results illustrative of the emission intensity of carbon at various plasma temperatures.
Figure 4:
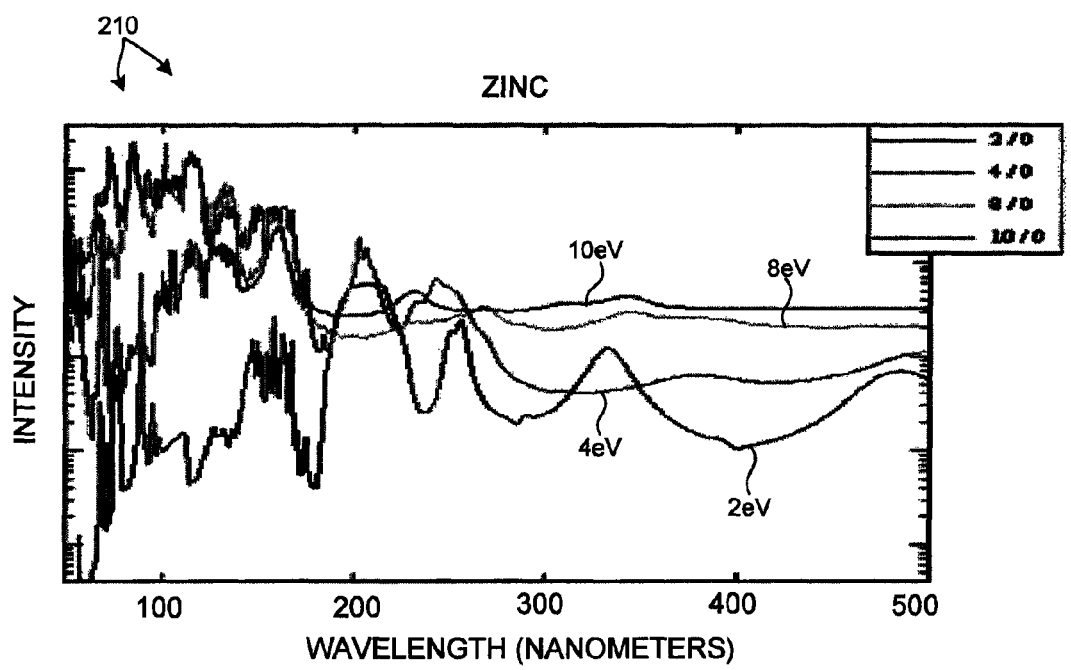
FIG. 4 is a plot of simulation results illustrative of the emission intensity of Zinc at various plasma temperatures.
Figure 5:
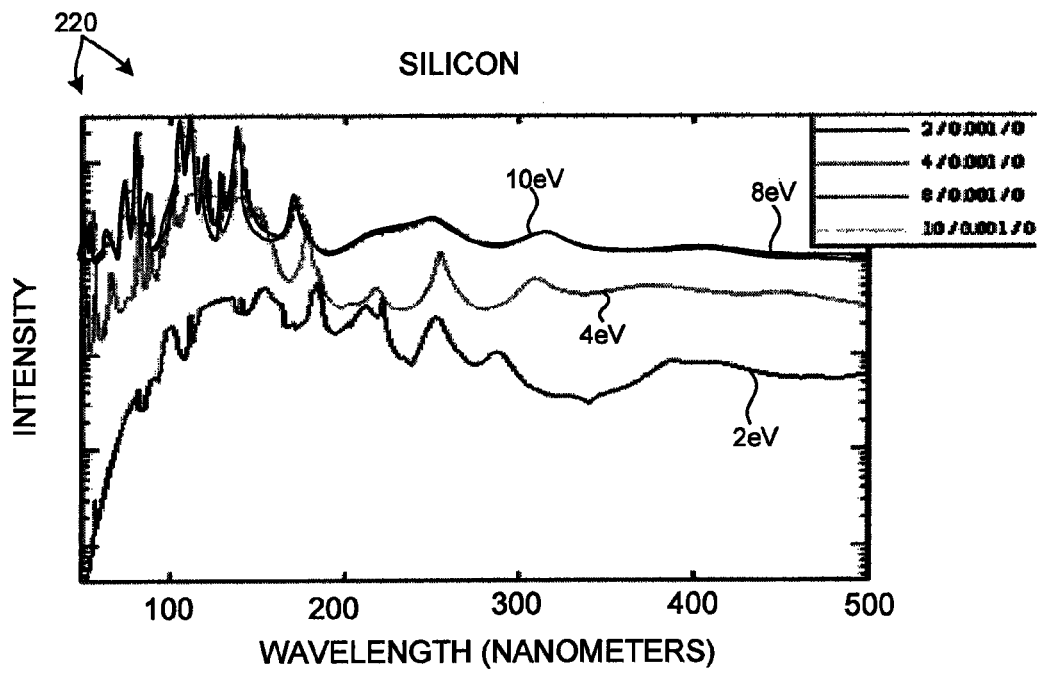
FIG. 5 is a plot of simulation results illustrative of the emission intensity of silicon at various plasma temperatures.
Figure 6:
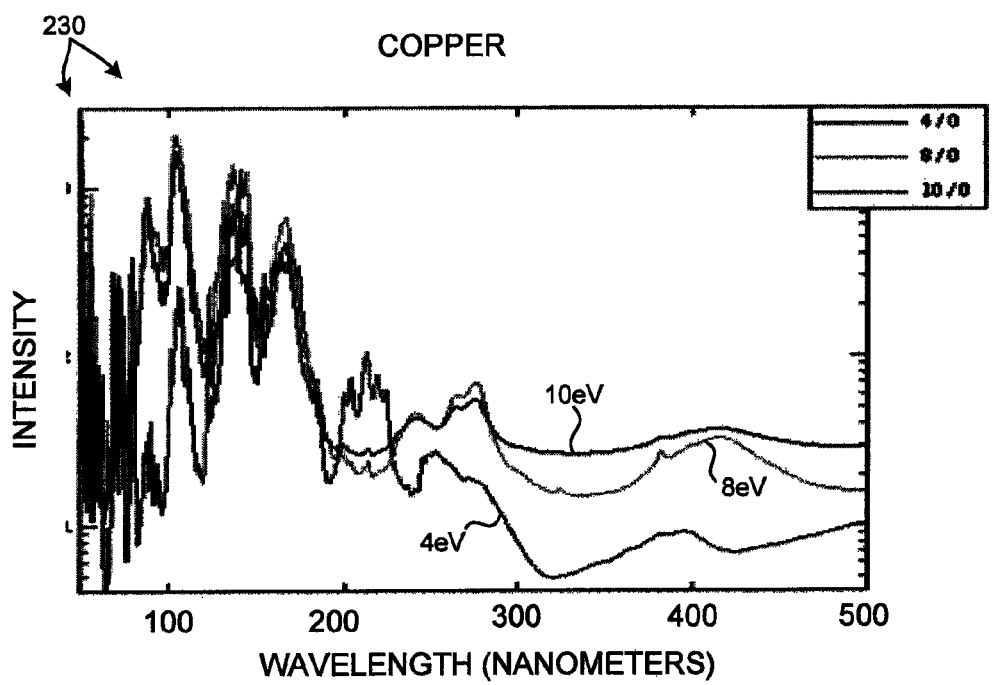
FIG. 6 is a plot of simulation results illustrative of the emission intensity of copper at various plasma temperatures.

By way of non-limiting example, FIGS. 3-6 illustrate different materials suitable as feed materials 112 to produce high radiance radiation from laser plasmas in the range of 100 nanometers to 200 nanometers. FIG. 3 illustrates a plot 200 of a simulated plasma emission spectrum of carbon. The intensity is plotted as a function of wavelength for plasma temperatures of 4 eV, 8 eV, and 10 eV. FIG. 4 illustrates a plot 210 of a simulated plasma emission spectrum of zinc. The intensity is plotted as a function of wavelength for plasma temperatures of 2 eV, 4 eV, 8 eV, and 10 eV. FIG. 5 illustrates a plot 220 of a simulated plasma emission spectrum of silicon. The intensity is plotted as a function of wavelength for plasma temperatures of 2 eV, 4 eV, 8 eV, and 10 eV at a plasma density of 1e-3 g/cm³. FIG. 6 illustrates a plot 230 of a simulated plasma emission spectrum of copper. The intensity is plotted as a function of wavelength for plasma temperatures of 4 eV, 8 eV, and 10 eV. All four materials illustrated in FIGS. 3-6 exhibit increasing emission in the range of 100 nanometers to 200 nanometers as the plasma temperature is increased. However, the conversion efficiency does not increase with plasma temperature. Copper, for example, exhibits higher conversion efficiency at 4 eV than either 8 or 10 eV. Also, zinc shows good conversion efficiency from 100 to 200 nanometers at 4 eV, but the wavelength for maximum emission shifts to below 150 nanometers as the temperature is increased to 8 eV and 10 eV. In this manner, the desired broadband emission spectrum of light source 110 may be tuned by varying the plasma temperature of a feed material.

In addition to carbon, silicon, zinc, and copper, a large variety of feed materials may be suitable to produce high radiance from laser plasmas in the range of 100 nanometers to 200 nanometers. For example, gallium, indium, oxygen, and arsenic may be suitable. In addition, a phosphate or a chloride may be doped (e.g., with water) to generate a droplet of suitable feed material. Similarly, metal halides and alkali metals may be doped to generate a droplet of suitable feed material. Suitable feed materials may include, but are not limited to Ga, In, C, Si, Zn, Cu, and O. In particular, suitable feed materials may include any of Ga, In, C, Si, Zn, Cu, and O in hydride or oxide molecular compositions. In one non-limiting example, suitable feed materials may include $SiH_4$, $SiO_2$, $O_2$, $CH_4$, $H_2O$, and $CO_2$. In other examples, suitable feed materials include the rare gases, the alkalis, and the halides.

To obtain an illumination light from a laser droplet plasma with a radiance greater than 10 w/mm$^2$-sr in a spectral region between 40 nanometers and 55 nanometers, a suitable material must be selected and the material must be heated to a sufficiently high plasma temperature at a sufficiently high plasma density.

Figure 7:
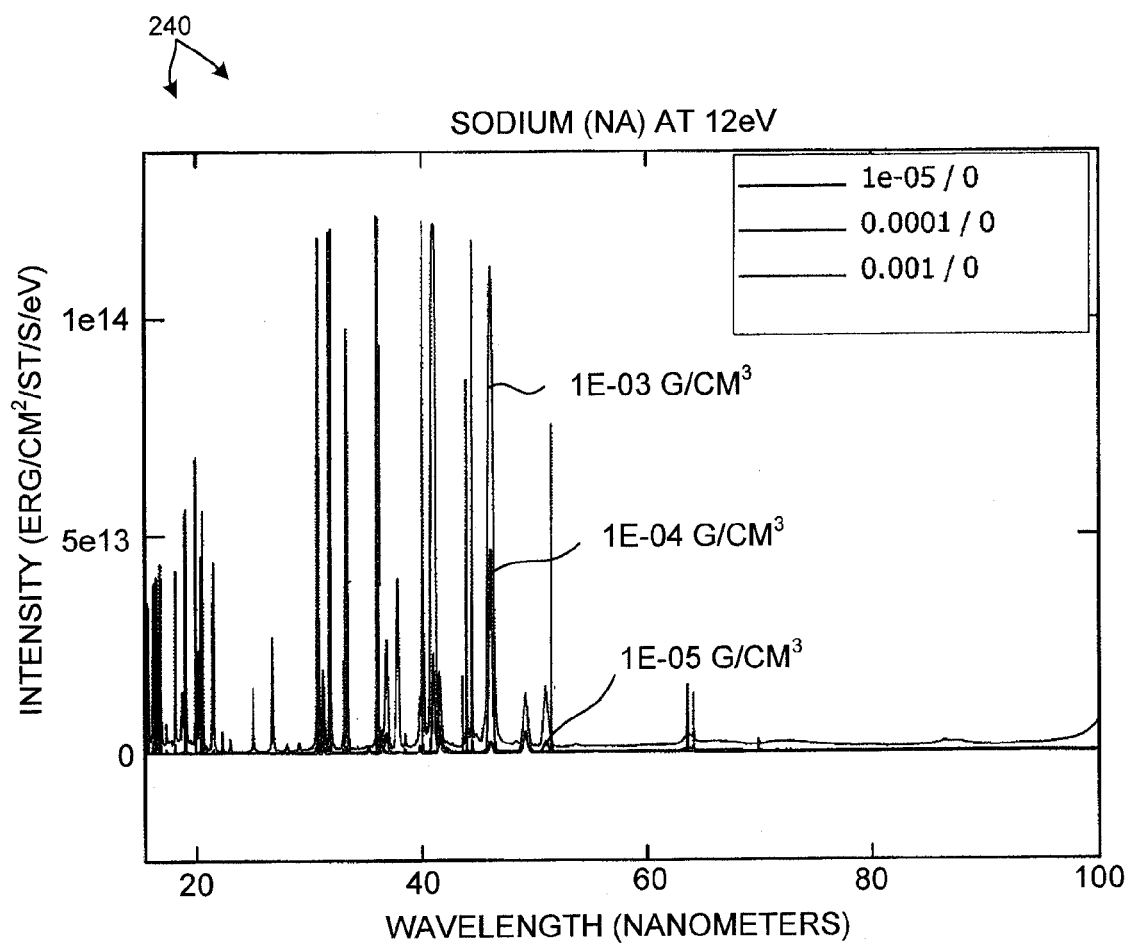
FIG. 7 is a plot of simulation results illustrative of the emission intensity of sodium at various plasma densities.
Figure 8:
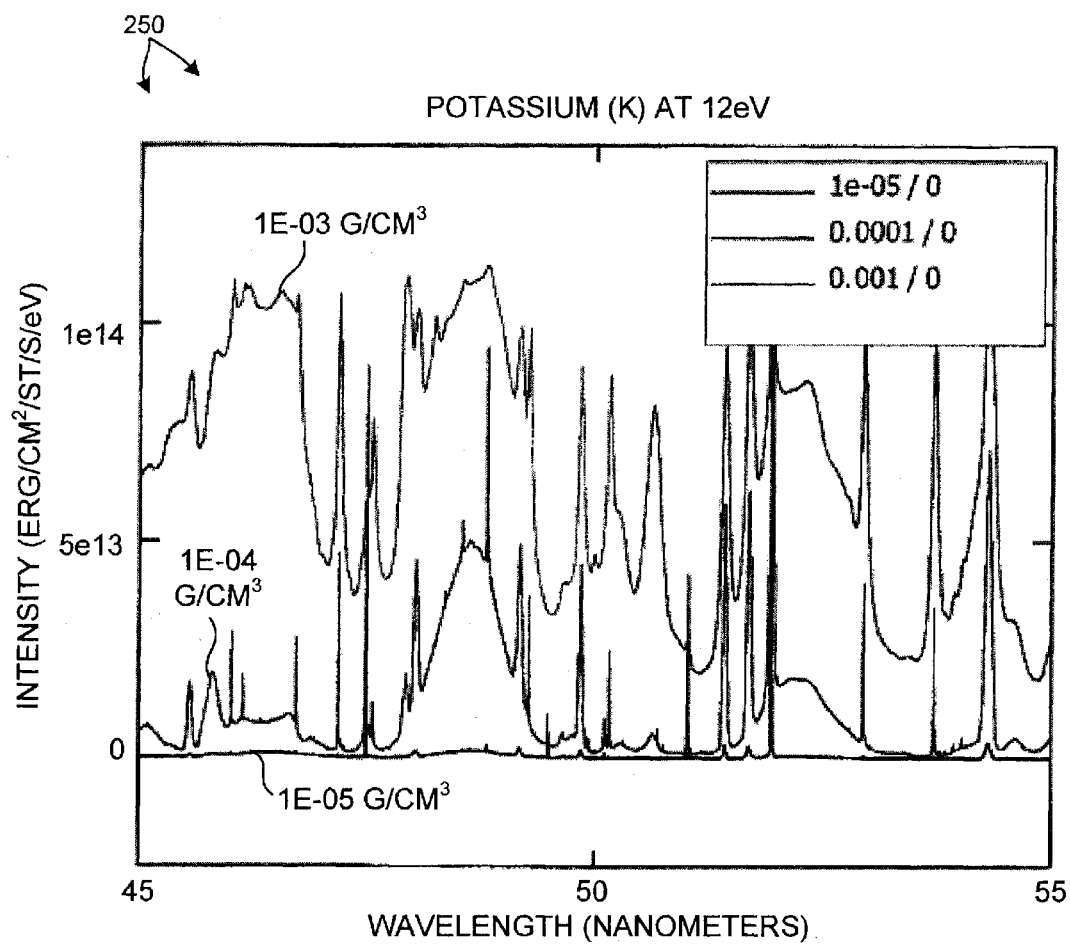
FIG. 8 is a plot of simulation results illustrative of the emission intensity of potassium at various plasma densities.
Figure 9:
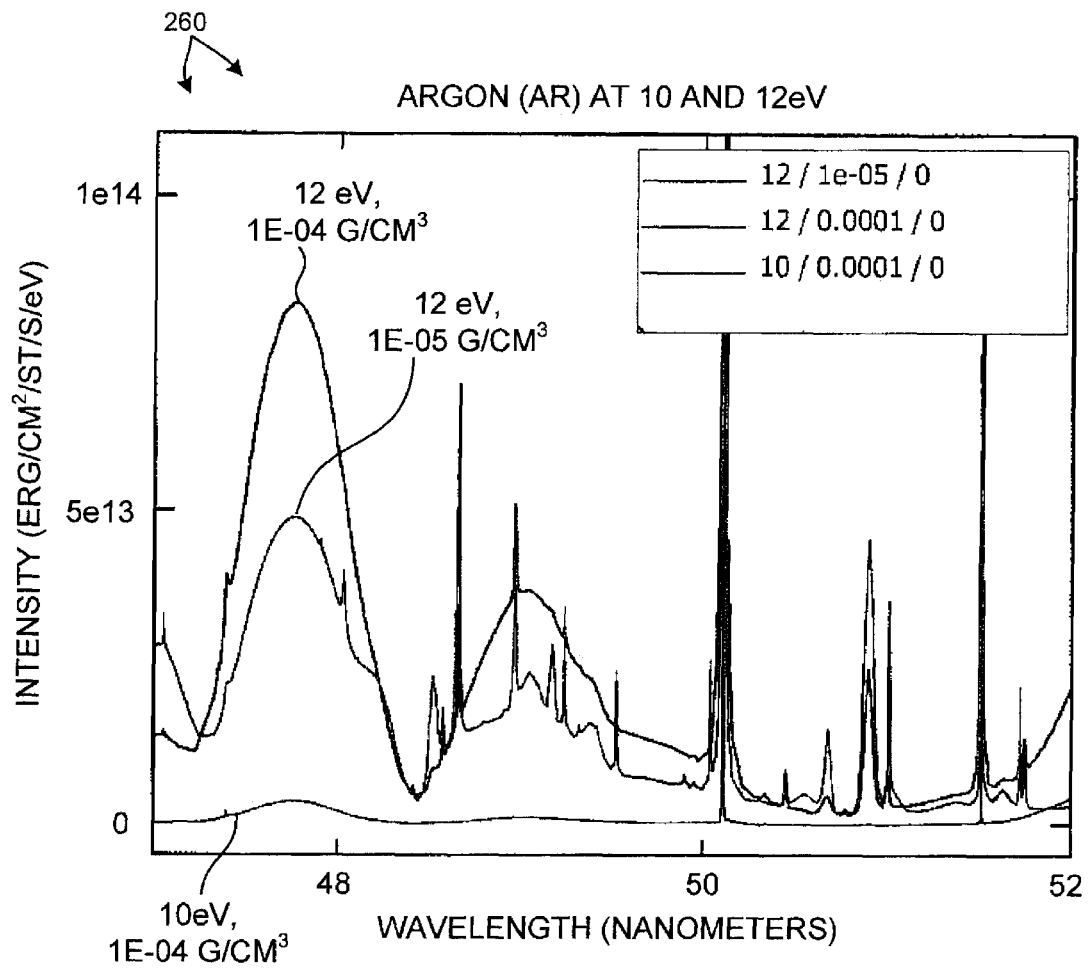
FIG. 9 is a plot of simulation results illustrative of the emission intensity of argon at various plasma temperatures and densities.
Figure 10:
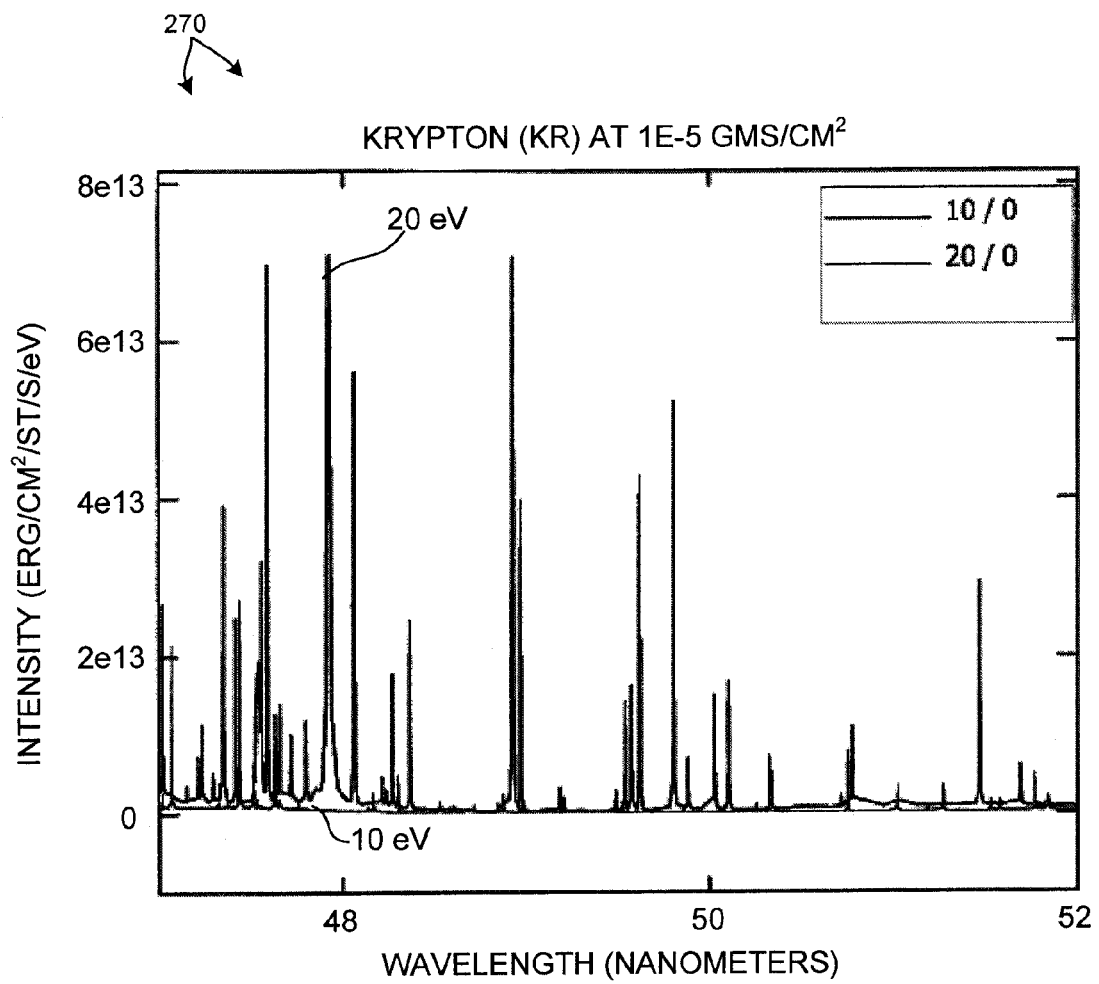
FIG. 10 is a plot of simulation results illustrative of the emission intensity of krypton at various plasma temperatures.

By way of non-limiting example, FIGS. 7-10 illustrate different materials suitable as feed materials 112 to produce high radiance from laser plasmas in the range of 40 nanometers to 55 nanometers. FIG. 7 illustrates a plot 240 of a simulated plasma emission spectrum of sodium. The intensity is plotted as a function of wavelength for plasma densities of 1e-3 grams/cm$^3$, 1e-4 grams/cm$^3$, and 1e-5 grams/cm$^3$ at a plasma temperature of 12 eV. FIG. 8 illustrates a plot 250 of a simulated plasma emission spectrum of potassium. The intensity is plotted as a function of wavelength for plasma densities of 1e-3 grams/cm$^3$, 1e-4 grams/cm$^3$, and 1e-5 grams/cm$^3$ at a plasma temperature of 12 eV. FIG. 9 illustrates a plot 260 of a simulated plasma emission spectrum of argon. The intensity is plotted as a function of wavelength for plasma densities of 1e-4 grams/cm and 1e-5 grams/cm at a plasma temperature of 12 eV and a plasma density of 1e-4 grams/cm$^3$ at a plasma temperature of 10 eV. FIG. 10 illustrates a plot 270 of a simulated plasma emission spectrum of krypton. The intensity is plotted as a function of wavelength for plasma temperatures of 10 eV and 12 eV at a plasma density of 1e-5 grams/cm$^3$. Potassium, sodium, and argon all exhibit useful amounts of emission in the range of 40 nanometers to 55 nanometers, particularly as the plasma density approaches 1e-5 grams/cm$^3$ and the plasma temperature approaches 12 eV. However, krypton must be driven to plasma temperatures approaching 20 eV to yield useful amounts of emission.

In addition to potassium, sodium, argon, and krypton, a large variety of feed materials may be suitable to produce high radiance radiation from laser plasmas in the range of 40 nanometers to 55 nanometers. For example, the metal halides and alkali metals are two families of practical feed materials for the production of radiation near 48 nm with plasma temperatures near between 8 and 20 eV. In addition, suitable feed materials may include, but are not limited to Ga, In, C, Si, Zn, Cu, and O. In particular, suitable feed materials may include any of Ga, In, C, Si, Zn, Cu, and O in hydride or oxide molecular compositions. In one non-limiting example, suitable feed materials may include $SiH_4$, $SiO_2$, $O_2$, $CH_4$, $H_2O$, and $CO_2$. In other examples, suitable feed materials include the rare gases.

As illustrated in FIG. 2, illumination light generated by light source 112 must interact with a number of optical components to effectively illuminate and image a wafer. At the present time refractive or transmissive optical components cannot be used to efficiently manipulate light in a spectral region between 40 nanometers and 200 nanometers. Light at these wavelengths is too readily absorbed by known transmissive materials. As a consequence, only reflective optical components are used to efficiently manipulate light in a spectral region between 40 nanometers and 200 nanometers within system 100. Furthermore, the per-surface reflectivity of each element must be held within a suitable range such that the detector 160 can gather sufficient image signal in high speed operation. In embodiments where light source 110 generates light between 100 nanometers and 200 nanometers, a bulk aluminum based, broad band coated optical objective, collector, zoom, and illumination sub-systems are suitable. In particular, $MgF_2$ overcoated aluminum mirrors deliver sufficient performance for wavelengths from 100-200 nm and longer.

In embodiments where light source 110 generates light between 40 nanometers and 55 nanometers, a Bragg mirror with stacks of multiple layers of pairs of materials with adequate reflectivity difference for 47 nanometer light is suitable. In addition, the material pairs must have suitably large skin depths at 47 nanometers so that the radiation at this wavelength is not significantly absorbed in the multiple (e.g., 40 or more) paired layers of the chosen materials. A Scandium/Silicon (Sc/Si) material pair has been demonstrated to deliver adequate reflectivity and sufficient bandwidth and therefore objective illumination angle tolerance for 47 nanometer light. Analysis of reflective coatings suitable to reflect radiation at these wavelengths is described in 1) "Enhanced reflectivity and stability of Sc/Si multilayers" by S. Yulin, F. Schafers, T. Feigl, and N. Kaiser, Advances in Mirror Technology for X-ray, EUV Lithography, Laser, and Other Applications in Proc. of SPIE, Vol. 5193 0277-786X (2004), the entirety of which is incorporated herein by reference, and 2) "Trimaterial multilayer coatings with high reflectivity and wide bandwidth for 25-50 nm extreme ultraviolet light," A. Aquila, F. Salmassi, Y. Liu, and E. Gullikson, Optics Express Vol. 17 (24), #117387 (2009), the entirety of which is incorporated herein by reference.

Collector 120 may be any suitable shape to gather illumination light generated from plasma 115. Suitable examples include elliptical collectors and collectors with multiple surface contours. Exemplary techniques for collecting light emitted from a plasma are described in U.S. Pat. No. 7,705,331, issued Apr. 27, 2010, to KLA-Tencor Technologies Corp., the entirety of which is incorporated herein by reference.

As depicted in FIG. 2, inspection system 100 includes a single laser focused directly on a droplet to generate plasma 115. However, inspection system 100 may include more than one laser with each laser configured differently or the same. For example, the lasers may be configured to generate light having different characteristics that can be directed to a droplet at the same or different times. In another example, the lasers may be configured to direct light to a droplet from the same or different directions. Exemplary techniques for directing excitation light to a target are described in the aforementioned U.S. Pat. No. 7,705,331, the entirety of which is incorporated herein by reference.

Illumination light may be transmitted by illumination optics 125. Illumination optics 125 may include a hollow optical homogenizer or a reflective light tube to efficiently transmit illumination light to a specimen or to the objective. Exemplary techniques for transmitting short wavelength light (e.g., light between 40 and 200 nanometers in wavelength) are described in International Patent Application No. PCT/US2010/039150 by applicant KLA-Tencor Corp. and published on Dec. 23, 2010 in International Publication No. WO 2010/148293 A2, the entirety of which is incorporated herein by reference.

A viable BF inspection system requires an imaging objective designed with an adequate field of view with distortions well within the imaging requirements permitted by the wafer inspection tool. As discussed above, a viable BF inspection system includes an objective 130 with a large NA. In some examples, the NA may be greater than 0.7. In other examples, the NA may be greater than 0.9. In addition to high NA, the light path through objective 130 should preferably include a minimum number of interactions with reflective surfaces to minimize absorption losses associated with each interaction. Exemplary designs for an objective with all reflective components using a four mirror, four pass design are described in U.S. Pat. No. 7,351,980, issued Apr. 1, 2008, to KLA-Tencor Technologies Corp., the entirety of which is incorporated herein by reference. In addition, exemplary designs for an objective with all reflective components using a four mirror, six pass design are described in U.S. patent application Ser. No. 12/568,483 assigned to Carl Zeiss SMT AG and published on Jul. 29, 2010, under U.S. Patent Publication No. 2010/0188738 A1, the entirety of which is incorporated herein by reference.

Illumination direction affects how a structure on a wafer is resolved by the inspection system 100. FIGS. 11-14 illustrate several examples of oblique illumination of wafer 140.

Figure 11A:
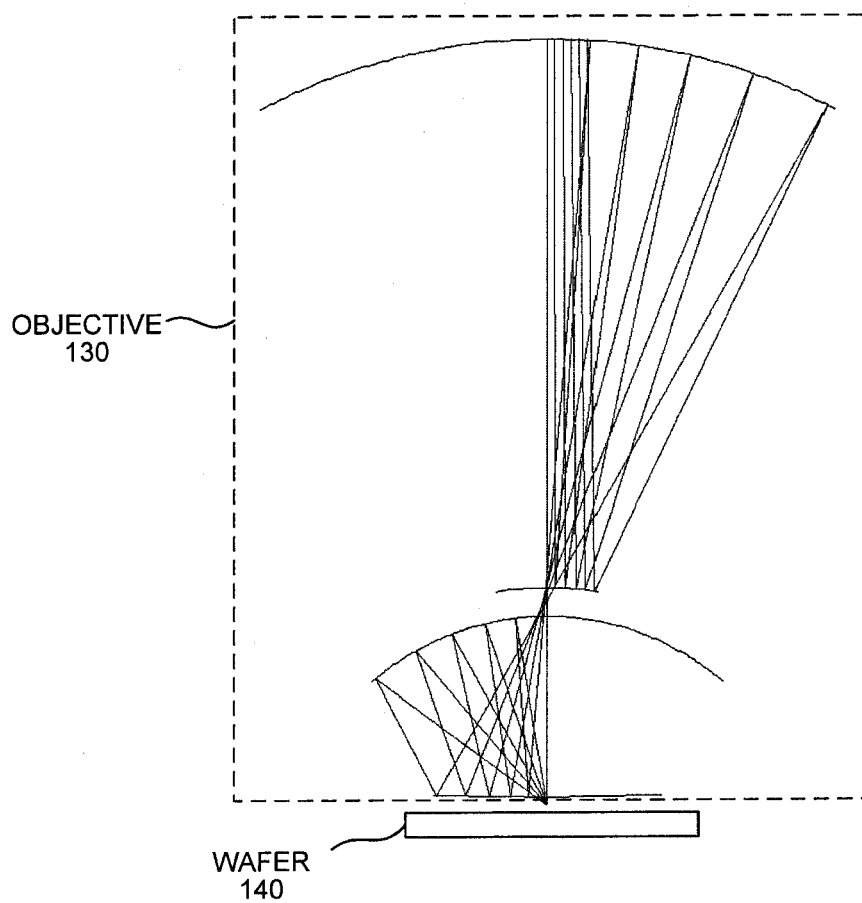
FIG. 11 is a simplified diagram illustrative of objective 130 where the illumination light 125 and the collected light 135 occupy spatially separated regions in the pupil plane 131.
Figure 11B:
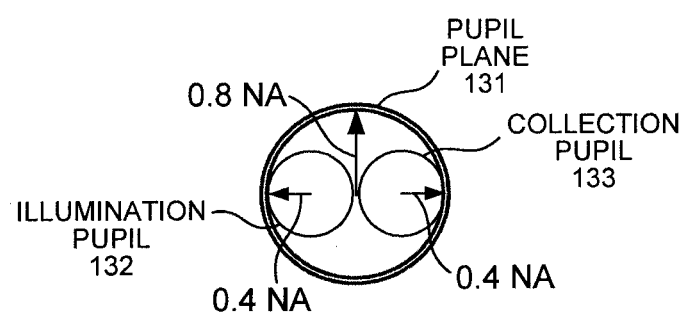

FIG. 11A illustrates an objective in a four mirror, four pass configuration. FIG. 11B illustrates a pupil plane 131 of objective 130. In this embodiment, objective 130 directs illumination light 125 to wafer 140 and gathers collected light 135 from wafer 140. However, the illumination light 125 and the collected light 135 occupy spatially separated regions in the pupil plane 131. As illustrated, the entirety of objective 130 has a NA of 0.8. Illumination pupil 132 represents a cross-sectional view of illumination light 125 passing through pupil plane 131. As illustrated the illumination NA is 0.4. Similarly, collection pupil 133 represents a cross-sectional view of collected light 135 passing through pupil plane 131. As illustrated, the imaging NA is 0.4. By keeping the collection pupil separated from the illumination pupil, obscuration is minimized, but at a cost of reduced NA for imaging. In addition, the illumination and collection can be moved around within the 0.8 objective NA.

Figure 12A:
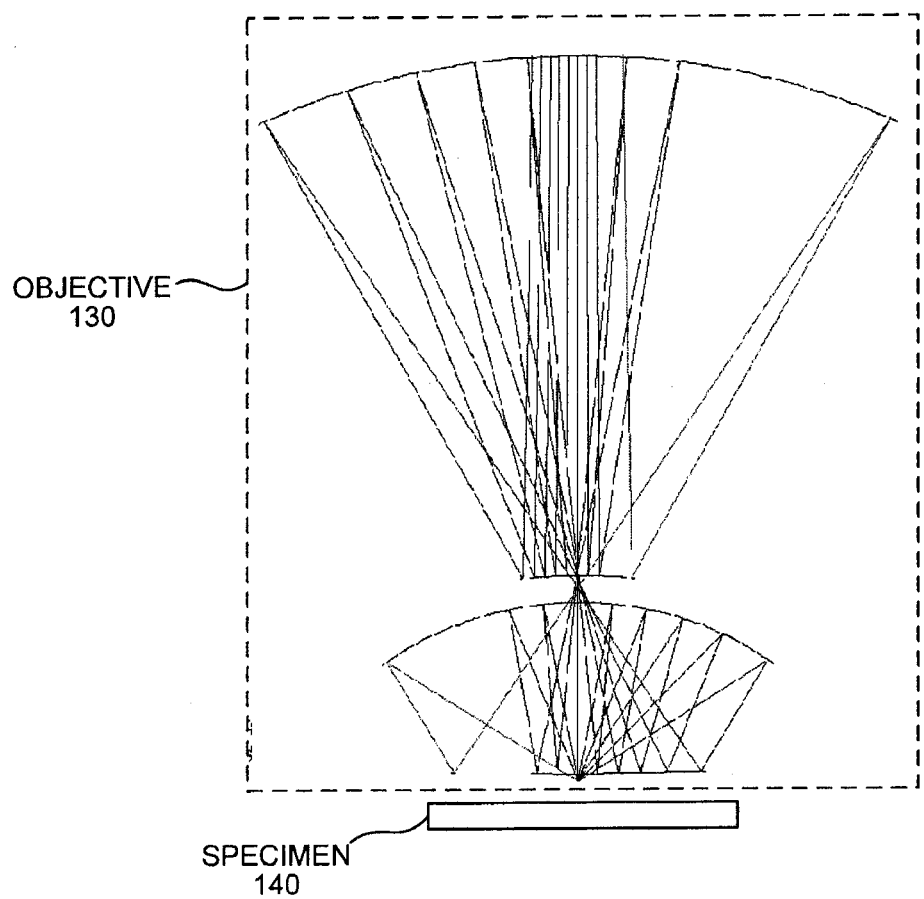
FIG. 12 is a simplified diagram illustrative of an objective 130 the illumination light 125 and the collected light 135 occupy spatially overlapping regions in the pupil plane 131.
Figure 12B:
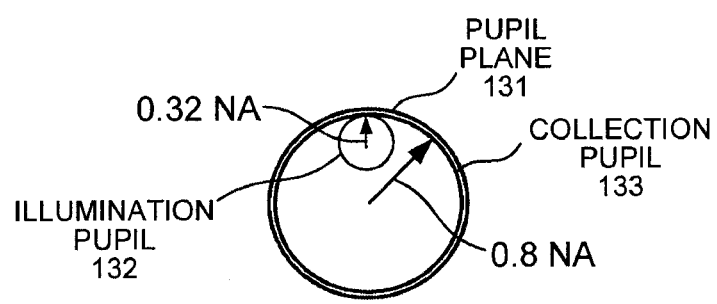

FIG. 12A illustrates an objective 130 in a four mirror, four pass configuration. FIG. 12B illustrates a pupil plane 131 of objective 130. In this embodiment, objective 130 directs illumination light 125 to wafer 140 and gathers collected light 135 from wafer 140. However, the illumination light 125 and the collected light 135 occupy spatially overlapping regions in the pupil plane 131. As illustrated, the entirety of objective 130 has a NA of 0.8. Illumination pupil 132 represents a cross-sectional view of illumination light 125 passing through pupil plane 131. As illustrated the illumination NA is 0.32. Similarly, collection pupil 133 represents a cross-sectional view of collected light 135 passing through pupil plane 131. As illustrated, the imaging NA is 0.8. However, by overlapping the collection pupil with the illumination pupil, beam-splitting between illumination and imaging needs to be used or obscuration occurs that limits the available NA for imaging.

Figure 13:
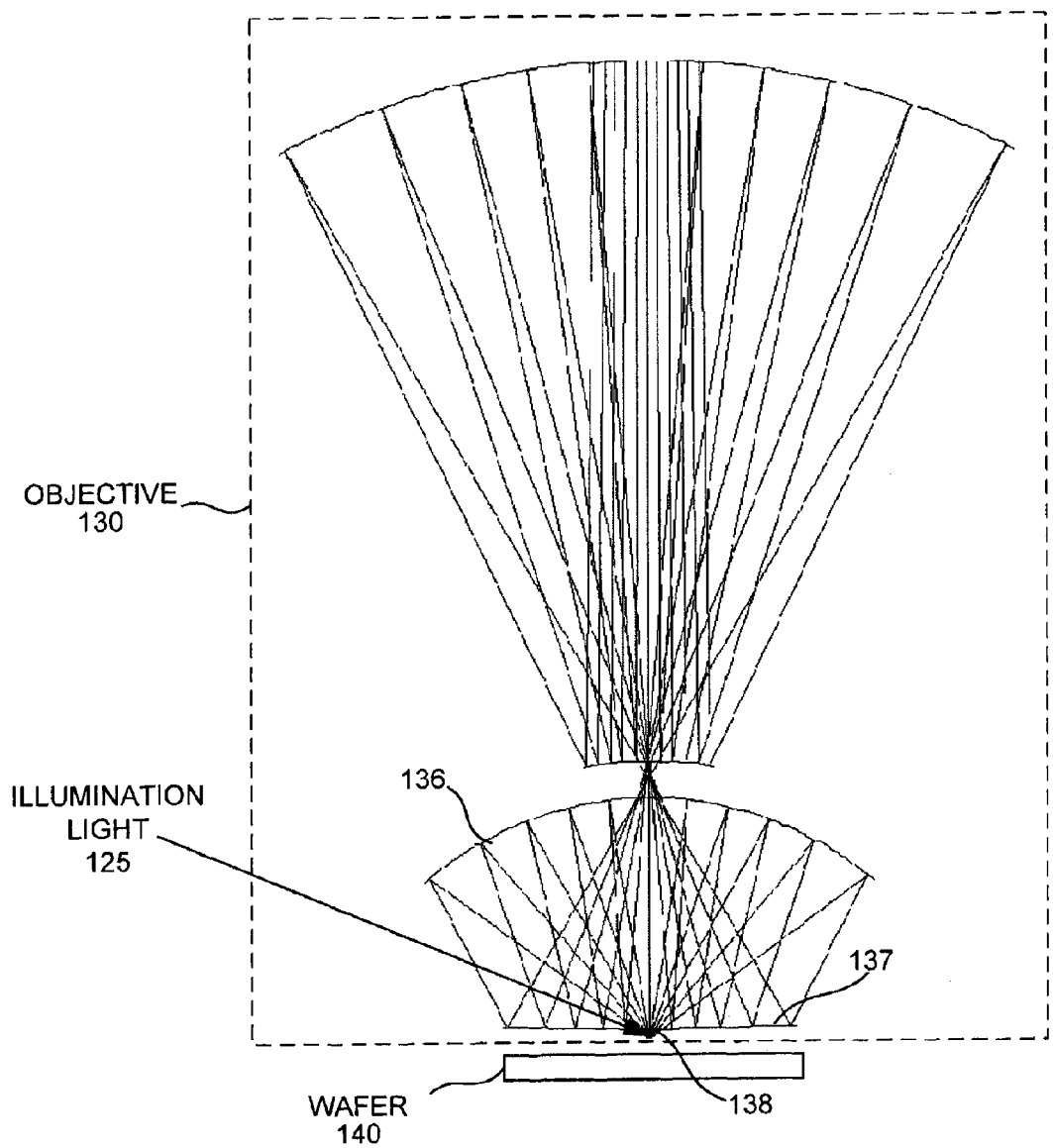
FIG. 13 is a simplified diagram illustrative of oblique injection of illumination light into objective 130 in a first embodiment.

FIG. 13 illustrates an objective 130 in a four mirror, four pass configuration. In this embodiment, illumination light 125 is obliquely inserted between reflective surfaces 136 and 137 of objective 130 and passes through aperture 138 of reflective surface 137 to wafer 140. In this manner, illumination light is directly transmitted to wafer 140 with only a very small amount of obscuration and almost the entirety of objective 130 available for imaging.

Figure 14:
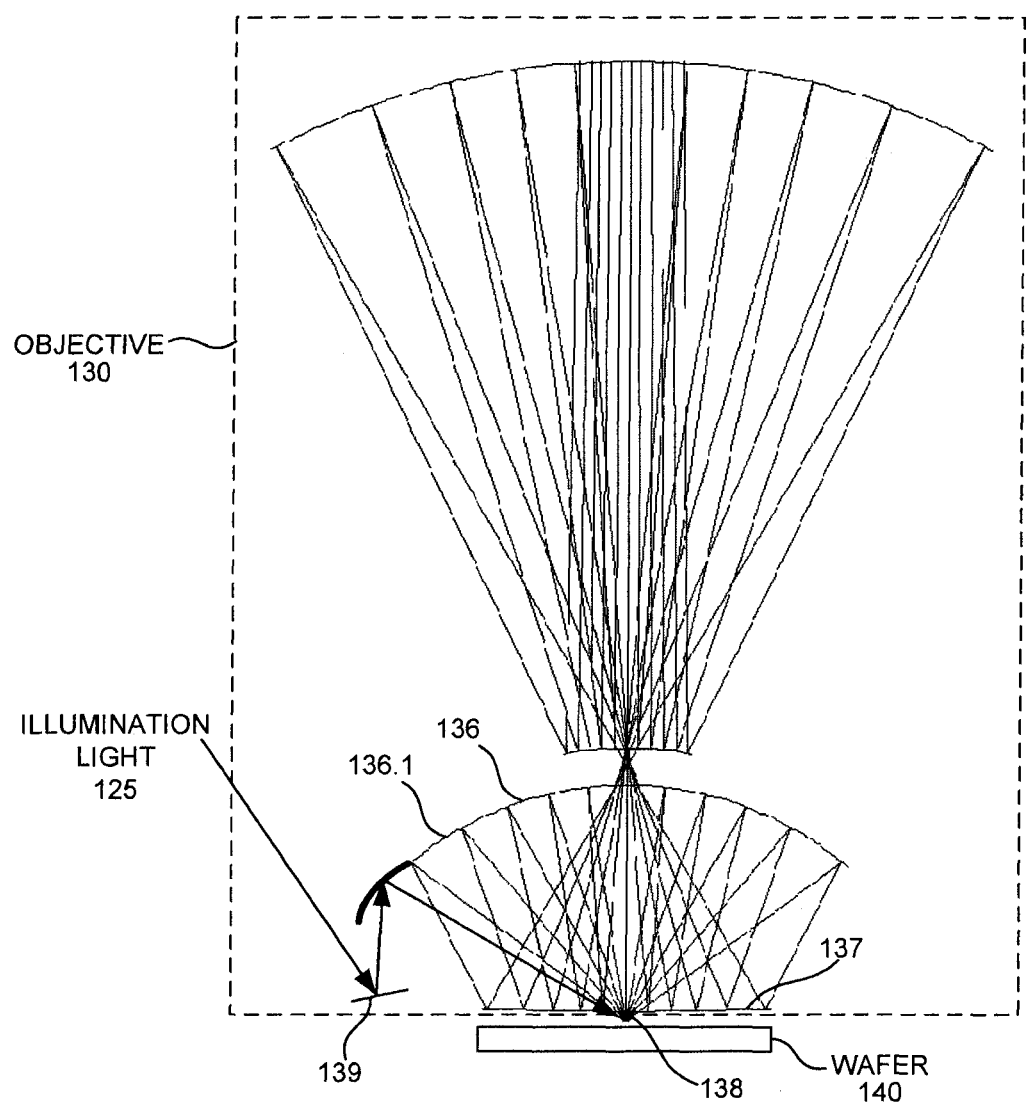
FIG. 14 is a simplified diagram illustrative of oblique injection of illumination light into objective 130 in a second embodiment.

FIG. 14 illustrates another example of oblique insertion of illumination light 125. In this embodiment, illumination light 125 is reflected off reflective element 139 to a portion 136.1 of reflective surface 136. Portion 136.1 may include a different surface geometry than other portions of reflective surface 136. Furthermore, in some examples, portion 136.1 is positioned such that it does not participate in the collection of light from wafer 140 by objective 130. Illumination light 125 incident to portion 136.1 is reflected and directed to wafer 140 through aperture 138. Thus, illumination light is obliquely inserted between reflective surfaces 136 and 137 of objective 130 and passes through aperture 138 of reflective element 137. In this manner, illumination light is directly transmitted to wafer 140 with only a very small amount of obscuration and almost the entirety of objective 130 is available for imaging.

In some embodiments, the optical configurations discussed above may have non-uniform optical properties in one of more of the reflective elements that are specifically optimized for illumination purposes. For example, coatings may be optimized to increase the coating durability due to the high exposure energy in the illumination path.

In one embodiment, detector 160 can be implemented with a plurality of TDI sensor modules. Each TDI sensor module can advantageously include localized circuitry for driving and signal processing. A module array including these TDI sensor modules can increase device manufacturability while decreasing driving and processing requirements relative to a large monolithic device of equivalent area. Exemplary TDI sensor modules and modular arrays are described in U.S. patent application Ser. No. 12/575,376, entitled "TDI Sensor Modules With Localized Driving And Signal Processing Circuitry For High Speed Inspection", which was filed by KLA-Tencor Corporation on Oct. 7, 2009 and is incorporated by reference herein.

Figure 15:
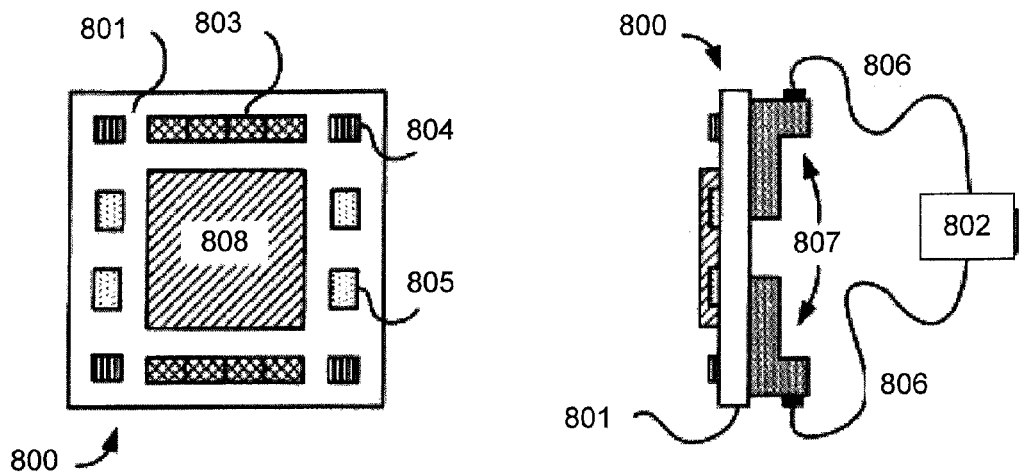
FIG. 15 is a diagram illustrative of an exemplary TDI sensor module that includes localized driving and signal processing circuitry.

FIG. 15 illustrates a top view of an exemplary TDI sensor module 800 that includes localized driving and signal processing circuitry (also called localized circuits herein). Specifically, TDI sensor module 800 includes a TDI sensor 802, processing circuits 803 for processing the signals from TDI sensor 802, timing and serial drive circuits 804, and pixel gate driver circuits 805.

In one embodiment, processing circuits 803 can provide correlated double sampling (CDS) and other analog front end (AFE) functions (e.g., analog gain control), analog to digital conversion (ADC), and digital postprocessing such as black-level correction, per pixel gain and offset corrections, linearity corrections, look-up tables (LUTs), and data compression. The processing may be fixed or rely on additional, possibly real-time, input from the inspection system to perform functions such as sub-pixel interpolation, analog gain control to prevent digital saturation, image position shifting, and image spatial distortion correction. In one embodiment, local processing circuits 803 can manipulate various captured images in the analog or digital domain (described in further detail below), thereby saving communication and processing bandwidth in an image analysis computer of the inspection system.

The timing and serial drive circuits 804 can control clock timing and drive for TDI. Features such as reset pulse generation, multi-phase serial-register clock generation, and ADC synchronization may be included. This allows for very accurate timing which is needed to achieve high SNR (signal to noise ratio) at high clocking speeds.

The pixel gate driver circuits 805 provide slower but higher-current TDI gate drive signals to synchronize data capture with the inspection image motion and with other TDI sensors. Pixel gate driver circuits 805 may typically provide three-phase or four-phase drive waveforms of square-wave and/or sinusoidal waveforms. More generally, pixel gate driver circuits 805 may use digital-to-analog conversion to provide arbitrary function generation in order to optimize the charge transfer, thermal dissipation, and SNR of the sensor. U.S. patent application Ser. No. 10/992,063, entitled "Continuous Clocking Of TDI Sensors", which is incorporated by reference herein, describes this digital-to-analog conversion in greater detail.

Advantageously, localized driving circuits mean that each TDI sensor module has its own individual set of drivers (i.e. driver 804 and 805). These individual drivers require significantly less current, and thus can be significantly smaller than conventional large-area TDI sensor drivers. Notably, locally distributing high fidelity, high-current waveforms from a plurality of small drivers (associated with the TDI sensor modules) is much more scalable than distributing waveforms from one large driver, even when the total current requirement is the same.

Figure 16:
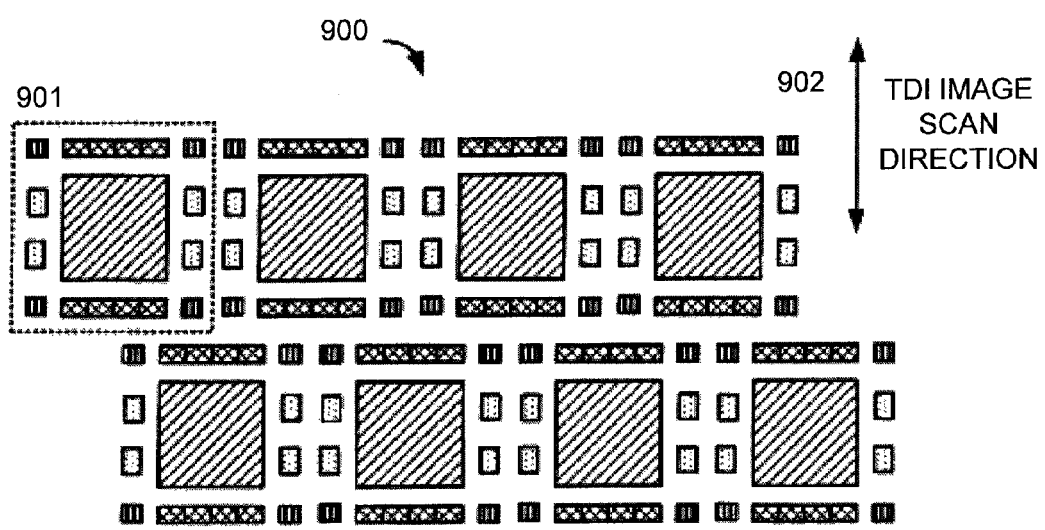
FIG. 16 is a diagram illustrative of an exemplary modular array of TDI sensor modules.

In one embodiment, each of processing circuits 803, timing and serial drive circuits 804, and pixel gate drive circuits 805 can be implemented on integrated circuits positioned around TDI sensor 802 on a PCB (printed circuit board) 801. Note that the number of ICs used to implement the driving/processing circuits can vary based on embodiment. In one embodiment, PCB 801 can be implemented using a multi-layer, ceramic substrate. FIG. 16 illustrates a side view of an exemplary PCB 801 including data transceivers 807 (e.g., 10 Gigabit optical transceivers) connected to PCB 801, wherein PCB 801 includes wiring (not shown for simplicity) in communication with the driving/processing circuits of TDI sensor module 800. Note that the PCB may also provide an ultra-high-vacuum interface for the sensor system and allow signals and power to pass between a high-quality vacuum region on the sensor side and a low-quality vacuum region or a region near atmospheric pressure on the fiber side. In one embodiment, optical fibers 806 can be attached to data transceivers 807 to allow communication of driving/processing data between TDI sensor module 800 and system-level inspection components 808. In another embodiment, digital data from TDI sensor module 800 can be transmitted off-board using low voltage differential signaling (LVDS), or similar electrical signaling and digital multiplexing. The specific protocol can be selected from an industry standard or prescribed by those sailed in the art of electronic or optical high-speed digital communications.

Figure 17:
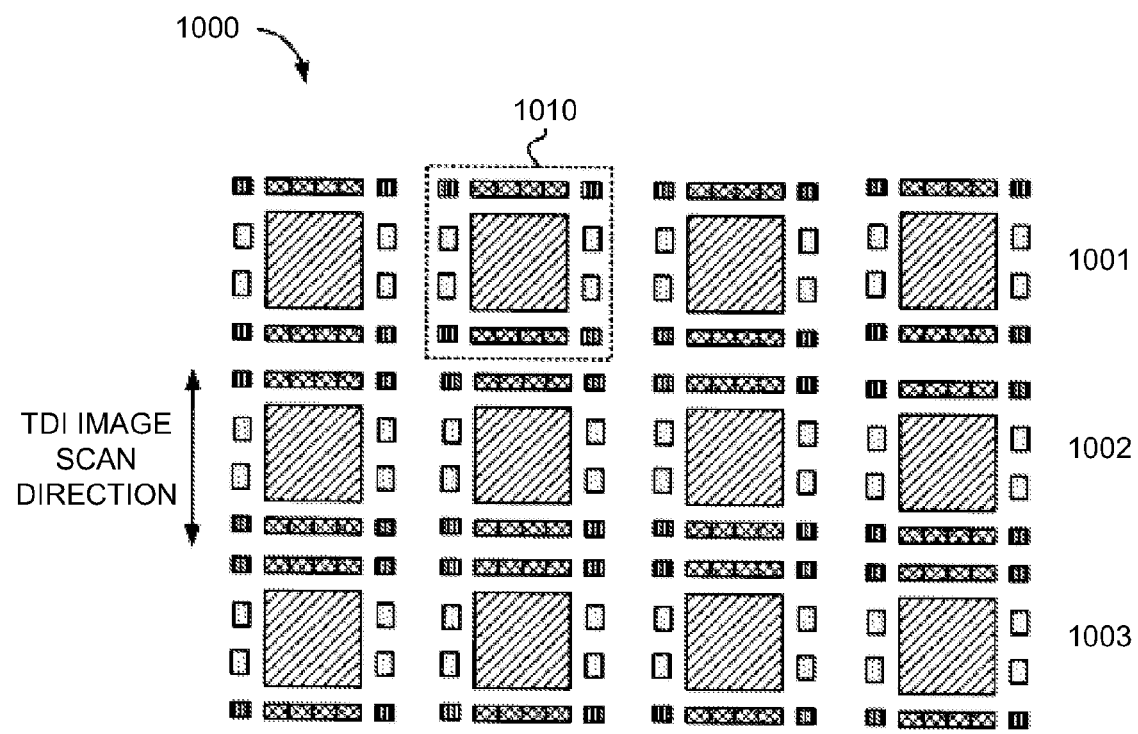
FIG. 17 is a diagram illustrative of an exemplary modular array of TDI sensor modules.

FIG. 17 illustrates an exemplary modular array 900 of TDI sensor modules 901 (also called a sensor module array). Note that the diving/processing circuits positioned around the TDI sensor take up a predetermined space. Thus, the TDI sensors in adjacent rows can be aligned such that at least 100% image coverage is achieved when used in a continuous scanning configuration. For example, an the embodiment shown in FIG. 17, the upper row can be offset with respect to the lower row such that the TDI sensor is positioned in the gap produced by the driving/processing circuits of an adjacent row. To ensure no gaps in image coverage, the width of each TDI sensor is equal to or greater than the space between TDI sensors. In this configuration, as the inspected wafer is being moved in a TDI image scan direction 902, sensor module array 900 can ensure complete image capture.

In one embodiment, some minimal overlap between TDI sensors from adjacent rows can provide redundant data. This redundant data can, for example, ensure accurate alignment of the image data generated by TDI sensor modules 901. In one embodiment of minimal overlap, the inspection system can arbitrarily select the data from one TDI sensor module to be used for the edge pixels. In another embodiment, a detection system can combine and align, using sub-pixel digital processing, the data from multiple TDI sensor modules, to achieve improved quality data near edge pixels.

Note that the effective data rate for modular array 900 can be significantly higher than a single, large TDI sensor. This rate is achieved because the modular array can have an effective total size and number of output channels that are larger than can be practically manufactured in a single TDI sensor. Further note that any number of rows of TDI sensor modules can be included in a modular array, i.e. TDI censor modules facilitate scaling. This scaling yields additional system flexibility and performance.

In another embodiment, integration of the detected data can be increased by aligning columns of the TDI sensor modules. For example, FIG. 17 illustrates an exemplary modular array 1000 including three rows 1001, 1002, 1003, and 1004 of TDI sensor modules 1010. In this embodiment, rows 1001-1003 capture and process samples of the same (or very similar) optical image data. Thus, modular array 1000 can advantageously provide a data stream for each swath of the inspected wafer. This integration can minimize the fluctuations associated with a plasma light source (inherently unstable because of its shot generation), which would otherwise cause inspection difficulties. This configuration can also reduce the uniformity and stability requirements of the plasma light source subsystem which improves the manufacturability and operating lifetime of the inspection system.

Other portions of the inspected surface missed by the gap between sensors in this embodiment can be inspected by a shift (left or right) of the wafer by the gap distance, and then performing another TDI image scan to cover another swath. This is called an interleave configuration. Note that the spacing between columns of the TDI sensor modules can be varied by compensating for the number of TDI image scans, i.e. the greater the spacing, the greater the number of TDI image scans (and thus, the number of swaths). Further note that even a single row of TDI sensor modules can be used in some embodiments, wherein the spacing between TDI sensor modules determines the number of swaths necessary to provide 100% inspection coverage.

One advantage of using modular arrays for inspection is that the inspected surface need only be partially illuminated. This dispersed illumination can advantageously also disperse the heat associated with the illumination, thereby allowing heat to more quickly dissipate to adjacent cooler areas and thus reduce the potential of damaging the inspected surface during high-speed inspection.

Another advantage of using modular arrays is an increased signal-to-noise ratio (SNR). Note that for visible light, the energy of the photon is generally sufficient to excite one electron into a conduction state. That is, one photon typically results in not more than one signal-generating electron. However, as the energy of the photon becomes higher, additional electrons can enter into a conduction state and be collected.

So, for a given TDI sensor electron well capacity per pixel, the maximum photon detection level is effectively reduced for short wavelength light (e.g., light in wavelength range of 40-200 nanometers). Also, because the image SNR for photon shot noise is proportional to the square root of the collected photons, the SNR will be reduced for short wavelength light.

The above-described modular array can advantageously improve the noise characteristics of the inspection system (i.e. the SNR). Specifically, having two TDI sensor modules collecting redundant image data can improve the SNR by a square root of two and, by extension, having N TDI sensor modules collecting redundant data can improve the SNR by a square root of N.

Note that although TDI sensor modules and TDI sensor arrays are described above in detail, the inspection system 100 can include sensor modules/arrays performing flash-on-the-fly mode (which generates a series of static images) or conventional CCD (charge coupled device) frame transfer readout instead of TDI.

Figure 18:
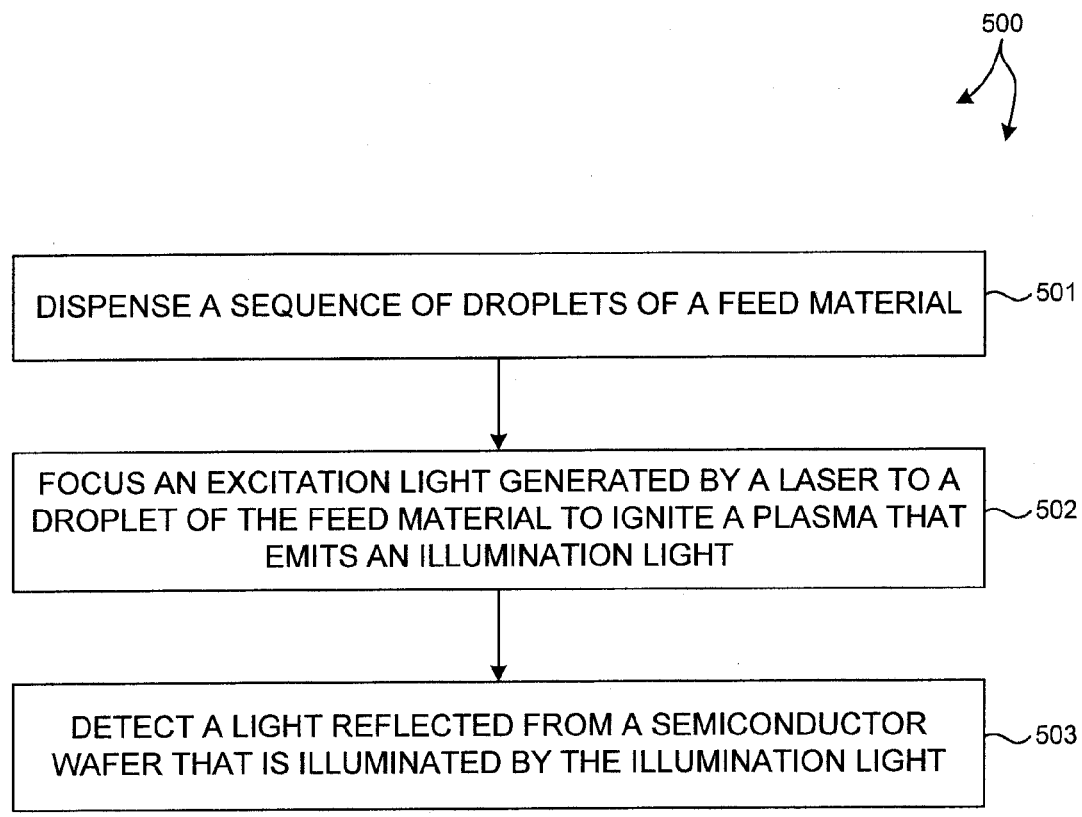
FIG. 18 is a flowchart of a method of inspecting a semiconductor wafer illuminated by an illumination light generated from a laser droplet plasma.

FIG. 18 illustrates a method 500 of inspecting a semiconductor wafer. In a first step (step 501), a sequence of droplets of a feed material is dispensed. In a second step (step 502), an excitation light generated by a laser is focused to a droplet of the feed material to ignite a plasma that emits an illumination light. In a third step (step 503), a light reflected from a semiconductor safer that is illuminated by the illumination light is detected.

As used herein, the term "specimen" generally refers to a wafer. However, it is to be understood that the methods and systems described herein may be used to provide illumination of any other specimen known in the art.

Although certain specific embodiments are described above for instructional purposes, the teachings of this patent document have general applicability and are not limited to the specific embodiments described above. For example, system 100 may include more than one light source (not shown). The light sources may be configured differently or the same. For example, the light sources may be configured to generate light having different characteristics that can be directed to a specimen at the same or different angles of incidence at the same or different times. The light sources may be configured according to any of the embodiments described herein. In addition one of the light sources may be configured according to any of the embodiments described herein, and another light source may be any other light source known in the art. Accordingly, various modifications, adaptations, and combinations of various features of the described embodiments can be practiced without departing from the scope of the invention as set forth in the claims.

What is claimed is:

1. An apparatus comprising:
    a light source comprising:
        a droplet generator that dispenses a sequence of droplets of a feed material; and
        a laser that generates an excitation light directed to a droplet of the feed material, wherein the interaction of the excitation light with the droplet of the feed material causes the droplet to ionize to form a plasma that emits an illumination light, wherein the illumination light comprises light in a spectral region from about 40 nanometers to about 200 nanometers, and wherein the illumination light is useable to illuminate a specimen.

2. The apparatus of claim 1, wherein the excitation light is generated by a solid state laser with a pulse duration between 1 nanosecond and 40 nanoseconds.

3. The apparatus of claim 2, wherein a wavelength of the excitation light is about one micron.

4. The apparatus of claim 2, wherein an energy of a pulse generated by the solid state laser is between 1 milliJoule and 20 milliJoules.

5. The apparatus of claim 2, wherein the solid state laser is taken from the group consisting of: a Ytterbium (Yb) based solid state laser and a Neodymium (Nb) based solid state laser.

6. The apparatus of claim 1, wherein the illumination light has a radiance of at least 10 W/mm2-sr within a spectral range from 40 nanometers to 55 nanometers.

7. The apparatus of claim 6, wherein the feed material includes any of a rare gas, an alkali metal and a metal halide.

8. The apparatus of claim 6, wherein the plasma reaches a temperature between 8 electron volts and 20 electron volts.

9. The apparatus of claim 1, wherein the illumination light has a radiance of at least 10 W/mm2-sr within a spectral range from 100 nanometers to 200 nanometers.

10. The apparatus of claim 9, wherein the feed material includes any of Ga, In, C, Si, Zn, Cu, and O in a hydride molecular composition or an oxide molecular composition.

11. The apparatus of claim 9, wherein the feed material is taken from the group consisting of: SiH4, SiO2, O2, CH4, H20, and CO2.

12. The apparatus of claim 9, wherein the plasma reaches a temperature between 4 electron volts and 10 electron volts.

13. The apparatus of claim 1, further comprising:
    a collector that gathers the illumination light emitted by the plasma that is useable to illuminate the specimen; and
    an objective that gathers and magnifies a collected light emitted from the specimen in response to the illumination light incident to the specimen and directs the collected light to a detector.

14. The apparatus of claim 13, wherein the objective directs the illumination light to the specimen, and wherein the illumination light and the collected light occupy spatially separated regions in a pupil plane of the objective.

15. The apparatus of claim 13, wherein the objective directs the illumination light to the specimen, and wherein the illumination light and the collected light occupy spatially overlapping regions in a pupil plane of the objective.

16. The apparatus of claim 13, further comprising:
    at least one illumination optic that directs the illumination light from the collector to the specimen, wherein a pupil plane of the objective includes only the collected light.

17. The apparatus of claim 13, further comprising:
    at least one illumination optic that directs the illumination light from the collector to at least one reflecting element of the objective that has a non-uniform optical profile, wherein a first portion of the element reflects the illumination light to the specimen, and wherein a second portion of the element gathers the collected light emitted from the specimen in response to the illumination light.

18. The apparatus of claim 13, wherein the detector is a silicon Time Delay and Integration (TDI) sensor.

19. The apparatus of claim 13, wherein a geometry of the plasma is sized to substantially match an etendue of the objective.

20. The apparatus of claim 1, wherein the specimen is a patterned semiconductor wafer.

21. A system for semiconductor wafer inspection comprising:
    a light source comprising:
        a droplet generator that dispenses a sequence of droplets of a feed material; and a laser that generates an excitation light directed to a droplet of the feed material, wherein the interaction of the excitation light with the droplet of the feed material causes the droplet to ionize to form a plasma that emits an illumination light, wherein the illumination light comprises light in a spectral region from about 40 nanometers to about 200 nanometers, and wherein the illumination light is useable to illuminate a specimen; and an objective that gathers and magnifies a collected light emitted from the specimen in response to the illumination light incident to the specimen and directs the collected light to a detector.

22. The system of claim 21, wherein the illumination light has a radiance of at least 10 W/mm2-sr within a spectral range from 40 nanometers to 55 nanometers.

23. The system of claim 22, wherein the objective comprises a plurality of reflective elements in an optical path of the collected light, and wherein the plurality of reflective elements are constructed of aluminum overcoated by MgF2.

24. The system of claim 21, wherein the illumination light has a radiance of at least 10 W/mm2-sr within a spectral range from 100 nanometers to 200 nanometers.

25. The system of claim 24, wherein the objective comprises a plurality of reflective elements in an optical path of the collected light, and wherein the plurality of reflective elements are coated with a Sc/Si material pair configured in a Bragg mirror arrangement.

26. A method of inspecting a semiconductor wafer, comprising:

dispensing a sequence of droplets of a feed material;

focusing an excitation light generated by a laser to a droplet of the feed material to ignite a plasma that emits an illumination light, wherein the illumination light comprises light in a spectral region from about 40 nanometers to about 200 nanometers, and wherein the illumination light is useable to illuminate a specimen; and detecting a light reflected from a semiconductor wafer illuminated by the illumination light.

27. A method comprising:

dispensing a sequence of droplets of a feed material; and focusing an excitation light generated by a laser to a droplet of the feed material to ignite a plasma that emits an illumination light with a radiance of at least 10 W/mm2-sr within a spectral range from 40 nanometers to 200 nanometers.

* * * * *